(12) United States Patent
Russak

(10) Patent No.: US 9,043,249 B2
(45) Date of Patent: May 26, 2015

(54) AUTOMATIC CHEMICAL ASSAY CLASSIFICATION USING A SPACE ENHANCING PROXIMITY

(75) Inventor: Ze'ev Russak, Ramat Gan (IL)

(73) Assignee: Azure Vault Ltd., Ramat Gan (IL)

( * ) Notice: Subject to any disclaimer, the term of this patent is extended or adjusted under 35 U.S.C. 154(b) by 501 days.

(21) Appl. No.: 13/510,186

(22) PCT Filed: Nov. 22, 2009

(86) PCT No.: PCT/IB2009/055277
§ 371 (c)(1),
(2), (4) Date: May 16, 2012

(87) PCT Pub. No.: WO2011/061568
PCT Pub. Date: May 26, 2011

(65) Prior Publication Data
US 2012/0239309 A1 Sep. 20, 2012

(51) Int. Cl.
*G06F 15/18* (2006.01)
*G06F 19/00* (2011.01)

(52) U.S. Cl.
CPC .................................. *G06F 19/707* (2013.01)

(58) Field of Classification Search
USPC ......................................... 706/12, 45, 20, 62
See application file for complete search history.

(56) References Cited

U.S. PATENT DOCUMENTS

| | | | |
|---|---|---|---|
| 6,503,720 B2 | 1/2003 | Wittwer et al. | |
| 6,564,153 B2 * | 5/2003 | Braun et al. | 702/22 |
| 6,783,934 B1 | 8/2004 | McMillan et al. | |
| 6,911,327 B2 | 6/2005 | McMillan et al. | |
| 2003/0041041 A1 | 2/2003 | Cristianini | |
| 2005/0084913 A1 * | 4/2005 | Punnonen et al. | 435/7.2 |
| 2006/0004753 A1 | 1/2006 | Coifman | |
| 2006/0224330 A1 | 10/2006 | Kurnik et al. | |
| 2007/0021929 A1 * | 1/2007 | Lemmo et al. | 702/22 |
| 2007/0073489 A1 | 3/2007 | Kurnik et al. | |

(Continued)

FOREIGN PATENT DOCUMENTS

| | | |
|---|---|---|
| JP | 2007-128483 | 5/2007 |
| WO | WO/03/029924 | 4/2003 |
| WO | WO/2007/113622 | 10/2007 |

OTHER PUBLICATIONS

Brechtbuehl et al., A rapid real-time quantitative polymerase chain reaction for hepatitis B virus. J Virol Methods. Apr. 2001;93(1-2):105-113.

(Continued)

*Primary Examiner* — David Vincent
(74) *Attorney, Agent, or Firm* — Michael A. Whittaker; Acuity Law Group, P.C.

(57) ABSTRACT

A computer implemented method for automatic chemical assay classification, the method comprising steps the computer is programmed to perform, the steps comprising: receiving a plurality of sets of parameters, each one of the received sets of parameters characterizing a respective assay of a chemical reaction, calculating a space enhancing proximity among points representative of assays of qualitatively identical chemical reactions, and representing each one of at least two of the received sets of parameters as a respective point in the calculated space, and dividing the points in the calculated space into a number of groups, according to proximity among the points in the calculated space, each group pertaining to a respective chemical reaction, thereby classifying the assays.

20 Claims, 13 Drawing Sheets

(56) References Cited

U.S. PATENT DOCUMENTS

| | | | |
|---|---|---|---|
| 2007/0073490 A1 | 3/2007 | Kurnik et al. | |
| 2007/0124088 A1 | 5/2007 | Woo et al. | |
| 2007/0129899 A1 | 6/2007 | Ward et al. | |
| 2007/0142315 A1* | 6/2007 | Forsbach et al. | 514/44 |
| 2007/0148632 A1 | 6/2007 | Kurnik et al. | |
| 2009/0119020 A1 | 5/2009 | Kurnik et al. | |
| 2009/0170091 A1* | 7/2009 | Giuliano et al. | 435/6 |
| 2009/0215991 A1* | 8/2009 | Lazar et al. | 530/387.1 |
| 2010/0233695 A1* | 9/2010 | Hayes et al. | 435/6 |
| 2011/0145176 A1* | 6/2011 | Perou et al. | 706/12 |

OTHER PUBLICATIONS

Brereton, Applied Chemometrics for Scientists. John Wiley and Sons LTD, UK, Copyright 2007, pp. 1-397.

Lee et al., ResonSense: simple linear fluorescent probes for quantitative homogenous rapid polymerase chain reaction. Analytica Chimica Acta 2002,;457:61-70.

Coifman and Lafon, Diffusion maps. Appl Comput Harmon Anal. Jun. 2006; 21:5-30.

International Search Report and Written Opinion of Jul. 15, 2010 in corresponding international application No. PCT/IB2009/055277.

International Preliminary Report on Patentability of May 22, 2012 in international application No. PCT/IB2009/055277.

Wold et al., "SIMCA: A method for analyzing chemical data in terms of similarity and analogy", Chemometrics Theory and Application, American Chemical Society Symposium 30 Series 52, Wash., D.C., American Chemical Society, pp. 243-282, Jun. 1, 1977.

Lafon et al. "Diffusion Maps", Applied and Computational Harmonic Analysis, vol. 21, Jul. 2006, pp. 5-30. Jun. 19, 2006.

Schechtman, "Inference in Two-Phase Regression: A Simulation study with Non-normal Observation", Journal of Statistical Computation and Simulation, vol. 17, issue 3, 1983, pp. 223-229.

Lee et al., "ReasonSense?: simple linear fluorescent probes for quantitative homogenous rapid polymerase chain reaction." Analytica Chimica Acta 2002, available on line Nov. 28, 2001, vol. 457, pp. 61-70.

Brechtbuehl et al., "A rapid real-time quantitative polymerase chain reaction for hepatitis B virus", Journal of Virological Methods, 2001,available on line Apr. 10, 2001, vol. 93, pp. 105-113.

* cited by examiner

AUTOMATIC CHEMICAL ASSAY CLASSIFICATION USING A SPACE ENHANCING PROXIMITY

FIELD AND BACKGROUND OF THE INVENTION

The present invention relates to analyzing chemical reactions and, more particularly, but not exclusively to systems and methods for automatic classification of assays of chemical reactions.

Monitoring chemical assays, in real time, through photometric measurements, such as real-time Polymerase Chain Reaction (PCR) and Quantitative Fluorescent Polymerase Chain Reaction (QF-PCR), produces a time series of values.

The values may be represented in a two dimensional graph depicting spectral changes over time, say of a real-time PCR based assay. The values may further be represented in a three dimensional graph depicting spectral changes vs. molecule length vs. time, say of a Capillary PCR based assay, etc., as known in the art.

For example, the spectral changes may include Fluorescence Intensity (FI) values measured over a PCR reaction apparatus, as known in the art. The measured FI values are indicative of the number of specific molecules detected in the PCR reaction.

The values measured may be used, to classify the kind of chemical reaction, which the assay involves.

For example, in QF-PCR, a graph representing the values measured over time may have linear properties, which indicate no amplification takes place. The graph may include a sigmoid curve interval, which indicates that a DNA amplification reaction occurs within the reaction apparatus.

Parameters extracted from the graph are used to determine the properties of the amplification. The right combination of parameters, say slopes of the graph in selected points, may indicate the existence of a specific subject, say existence of a specific bacterial DNA sequence.

In Capillary PCR, DNA fragments length is used to determine the DNA structure. Capillary PCR may further indicate existence or absence of known fragment patterns, or variation from certain known patterns. The patterns may indicate the existence, absence or mutation, of a specific Gene.

In RT-PCR (Reverse-Transcriptase PCR), one of the above mentioned methods, may be used, to determine Gene Expression, under specific conditions.

With Gene Expression there is found whether a certain DNA sequence (i.e. a certain gene) may be used for manufacturing RNA (say using Qf-RT-PCR), or the structure of the manufactured RNA.

Traditionally, the classification of the assays is based on manual examination by an expert in the field. The expert manually examines hundreds or thousands of samples (say thousands of graphs derived from QF-PCR based assays), detects certain features in the samples, and classifies each sample to one of two or more groups of chemical reactions.

Some currently used methods provide for automatic detection of certain features in chemical reactions, such as PCR.

For example, US Patent Publication No. 20070148632, to Kurnik et al., describes Systems and methods for determining characteristic transition values such as elbow values in sigmoid or growth-type curves, utilizing a Levenberg-Marquardt (LM) regression processes.

U.S. patent application Ser. No. 11/861,188, to Kurnik et al., filed on Sep. 25, 2007, entitled "PCR elbow determination using curvature analysis of a double sigmoid", describes a method utilizing a first or second degree polynomial curve that fits the a growth type curve, and determination of a statistical significance value for the curve fit. The significance value indicates whether the data represents significant or valid growth.

Some of the currently used methods are based on a multi-variant statistical model.

For example, PCT Patent Application No.: PCT/IB2006/051025, filed on Apr. 4, 2006, to Tichopad et al., entitled "Assessment of Reaction Kinetics Compatibility between Polymerase Chain Reactions", describes the usage of a large training set, to statistically compare properties of chemical assays.

Similarly, Wold et al, describe in a 1977 article, entitled "SIMCA: A method for analyzing chemical data in terms of similarity and analogy", in Kowalski, B. R., ed., Chemometrics Theory and Application, American Chemical Society Symposium Series 52, Wash., D.C., American Chemical Society, p. 243-282, a method which requires availability of a large training data set of samples, with a set of attributes and class memberships.

The above described methods rely on a training set built manually, by an expert. In order to build the training set, the expert has to manually examine hundreds or thousands of samples. The expert further has to classify each sample into one of two or more groups of chemical reactions.

The manual classification of the assays may also be based on a set of logical conditions, used to validate a new sample, against a constructed list of decisions, say using a decision tree, as known in the art.

SUMMARY OF THE INVENTION

According to one aspect of the present invention there is provided a computer implemented method for automatic chemical assay classification. The method comprises steps the computer is programmed to perform.

The steps comprise receiving a plurality of sets of parameters, each one of the received sets of parameters characterizing a respective assay of a chemical reaction, calculating a space enhancing proximity among points representative of assays of qualitatively identical chemical reactions, and representing each one of at least two of the received sets of parameters as a respective point in the calculated space, and dividing the points in the calculated space into a number of groups, according to proximity among the points in the calculated space, each group pertaining to a respective chemical reaction, thereby classifying the assays.

According to a second aspect of the present invention there is provided a method for automatic chemical assay classification, the method comprising steps of: performing a plurality of assays of chemical reactions, extracting a set of parameters from each of the assays, calculating a space enhancing proximity among points representative of assays of qualitatively identical chemical reactions, and representing each one of at least two of the extracted sets of parameters as a respective point in the calculated space, and dividing the points in the calculated space into a number of groups, according to proximity among the points in the calculated space, each group pertaining to a respective chemical reaction, thereby classifying the assays.

According to a third aspect of the present invention there is provided an apparatus for automatic chemical assay classification, the apparatus comprising: a parameter receiver, configured to receive a plurality of sets of parameters, each one of the received sets of parameters characterizing a respective assay of a chemical reaction, a space calculator, in communication with the parameter receiver, configured to calculate a space enhancing proximity among points representative of assays of qualitatively identical chemical reactions, and to represent each one of at least two of the received sets of parameters as a respective point in the calculated space, and a classifier, in communication with the spaces calculator, configured to divide the points in the calculated space into a number of groups, according to proximity among the points in the calculated space, each group pertaining to a respective chemical reaction, thereby classifying the assays.

According to a fourth aspect of the present invention there is provided an apparatus for automatic chemical assay classification, the apparatus comprising: a chemical reaction apparatus, configured to perform a plurality of assays of chemical reactions, a parameter extractor, connected to the chemical reaction apparatus, configured to extract a set of parameters from each of the performed assays, a space calculator, in communication with the parameter receiver, configured to calculate a space enhancing proximity among points representative of assays of qualitatively identical chemical reactions, and to represent each one of at least two of the extracted sets of parameters as a respective point in the calculated space, and a classifier, in communication with the spaces calculator, configured to divide the points in the calculated space into a number of groups, according to proximity among the points in the calculated space, each group pertaining to a respective chemical reaction, thereby classifying the assays.

According to a fifth aspect of the present invention there is provided a computer readable medium storing computer executable instructions for performing steps of automatic chemical assay classification, the steps comprising: receiving a plurality of sets of parameters, each one of the received sets of parameters characterizing a respective assay of a chemical reaction, calculating a space enhancing proximity among points representative of assays of qualitatively identical chemical reactions, and representing each one of at least two of the received sets of parameters as a respective point in the calculated space, and dividing the points in the calculated space into a number of groups, according to proximity among the points in the calculated space, each group pertaining to a respective chemical reaction, thereby classifying the assays.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit.

As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings.

DESCRIPTION OF THE PREFERRED EMBODIMENTS

Figure 1:
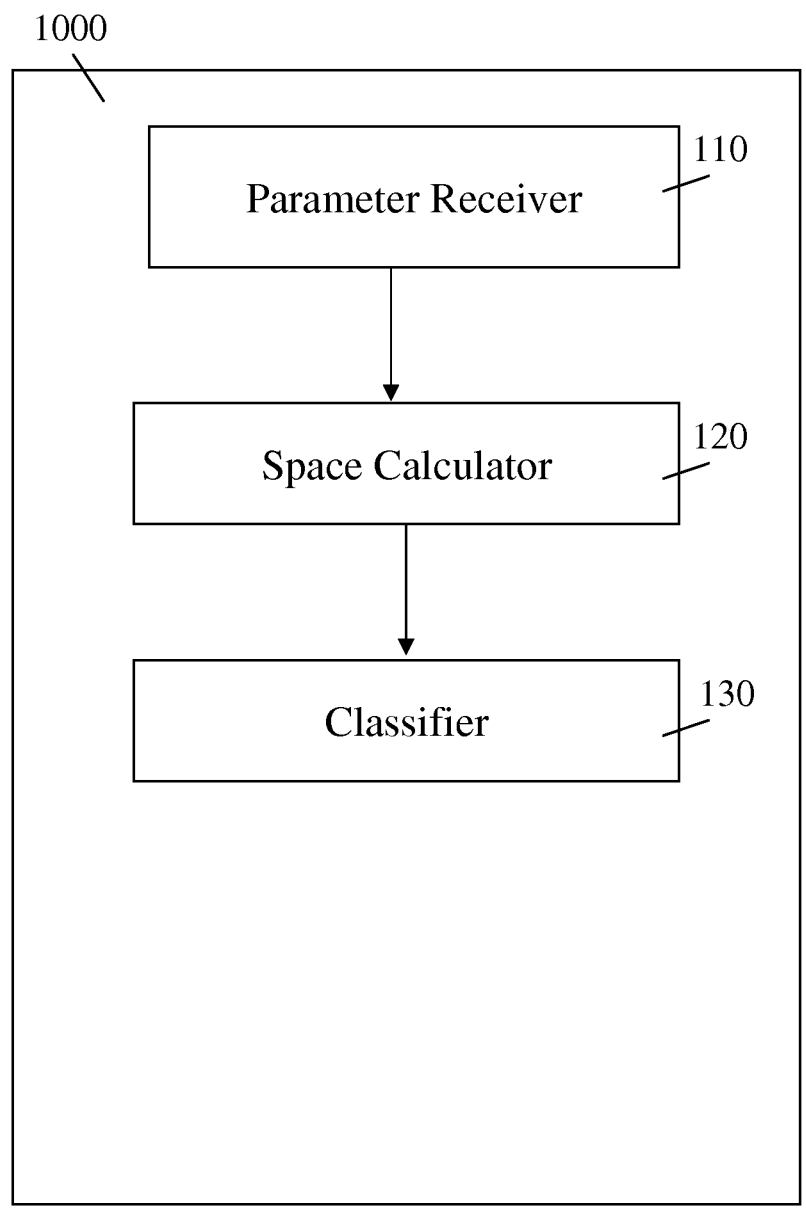
FIG. 1 is a block diagram schematically illustrating a first apparatus for automatic chemical assay classification, according to an exemplary embodiment of the present invention.

The present embodiments comprise a system and apparatus for automatic chemical assay classification.

According to an exemplary embodiment of the present invention, there are received sets of parameters derived from an assay of a chemical reaction (such as PCR).

The parameters may include, but are not limited to: Fluorescence Intensity (FI) value of one or more elbow points of a sigmoid graph depicting the chemical reaction, a time of each of the elbow points, Fluorescence Intensity (FI) values at certain points of the sigmoid graph, etc., as described in further detail hereinbelow.

Parameters derived from a single type of reaction may assume a wide range of kinetic properties. Hence, in a Euclidian space, data points that represent assays of chemical reactions of the same type may be scattered over a large area. That is to say that a Euclidean distance between two data points, which represent assays of the same type of a chemical reaction, may be greater than a Euclidean distance between two data points which represent assays of different chemical reaction types.

According to an exemplary embodiment of the present invention, there is calculated a space which, unlike the Euclidian space, tends to enhance proximity among points representative of assays of qualitatively identical chemical reactions.

Qualitatively identical chemical reactions include reactions which involve the same major reactant of interest. Qualitatively identical chemical reactions may include, but are not limited to: Polymerase Chain Reactions, in which the same DNA sequence is found (though not necessarily in the same quantity or concentration), forensic chemical tests, in which different traces of the same explosive material are assayed, etc., as known in the art.

Methods which are usable for calculating the space may include, but are not limited to: Dimensionality Reduction, Diffusion Mapping and Kernel Principal Component Analysis (Kernel PCA), as described in further detail hereinbelow.

Each of the received sets of parameters may be represented in the calculated space as a point in the calculated space.

The points in the calculated space are divided into a number of groups, according to proximity among the points in the calculated space. Each of the groups pertains to a respective type of qualitatively identical chemical reactions.

Consequently, the assays are classified into the groups of qualitatively identical chemical reactions, as described in further detail hereinbelow.

The principles and operation of a system and method according to exemplary embodiments of the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a block diagram schematically illustrating a first apparatus for automatic chemical assay classification, according to an exemplary embodiment of the present invention.

Apparatus 1000 for automatic chemical assay classification may be implemented using electric circuits, computer instructions, etc. The apparatus 1000 may be implemented on a dedicated computer, on a computer chip connectable to a laboratory device (say to a PCR apparatus, as known in the art) or installable thereon, on a computerized controller (say a computerized controller used in a chemical factory), etc.

Optionally, the chemical reaction is a Polymerase Chain Reaction (PCR), say a Quantitative Fluorescent Polymerase Chain Reaction (QF-PCR), as described in further detail hereinabove.

Apparatus 1000 includes a parameter receiver 110.

The parameter receiver 110 receives sets of parameters. Each of the received sets of parameters characterizes a specific assay of a chemical reaction.

The received parameters may include, but are not limited to: photometric measurement values such as Fluorescence Intensity (FI) values of one or more elbow points of a sigmoid graph depicting the assay of the chemical reaction, a time of each of the elbow points, Fluorescence Intensity (FI) values of certain points of the sigmoid graph, etc., as described in further detail hereinbelow.

Optionally, the parameters include Euclidian Coordinate Values of one or more elbow points of the chemical reaction, as depicted by a graph.

Optionally, the parameters include Euclidian Coordinate Values of one or more EC50 points of the chemical reaction, as depicted by a graph. An EC50 point is a point halfway between the baseline and maximum of the chemical reaction, as known in the art.

Apparatus 1000 further includes a space calculator 120, in communication with the parameter receiver 110.

The space calculator 120 calculates a space which, unlike a Euclidean space, enhances proximity among points representative of assays of qualitatively identical chemical reactions. The space calculator 120 further represents each one of two or more of the received sets of parameters, as a respective point in the calculated space.

Methods which may be used by the space calculator 120, for calculating of the space include, but are not limited to: Dimensionality Reduction, Diffusion Mapping and Kernel Principal Component Analysis (Kernel PCA), as described in further detail hereinbelow.

Apparatus 1000 further includes a classifier 130, in communication with the parameter receiver 110.

The classifier 130 divides the points in the calculated space into a number of groups, according to proximity among the points in the calculated space, each group pertaining to a respective chemical reaction, thereby classifying the assays.

Optionally, the classifier 130 uses k-means clustering, for dividing the points in the calculated space, into the number of groups.

K-Means Clustering is a method of cluster analysis, which aims at partitioning observations into k clusters (i.e. groups), as described in further detail hereinbelow.

Optionally, the apparatus 1000 also includes a parameter extractor, in communication with the parameter receiver 110.

The parameter extractor extracts the parameters from the assay of the chemical reaction, as described in further detail hereinbelow.

Optionally, the parameter extractor extracts the parameters, using current methods, usable for extracting parameters from a graph which depicts the assay of the chemical reaction, such as PCR, as described in further detail hereinabove.

Optionally, in order to verify that the groups are not intertwined, the classifier 130 further finds a first point. The first point is a point nearest to a center of a first one of the groups, among all points of the first group.

The classifier 130 may also receive first data identifying a chemical reaction of the first point.

The first data may include, but is not limited to: data obtained by microbiological testing of the materials used for the assay, data obtained by inspection through a microscope, data extracted using an additional chemical reaction, etc., as known in the art.

The classifier 130 may also find a second point. The second point is a point nearest to a center of a second one of the groups, among all points of the first group.

The classifier 130 may also receive second data identifying a chemical reaction of the second point.

Upon the first and second data indicating a qualitative difference between the chemical reactions of the found points, the classifier 130 divides the points (already divided into the number of groups) into a higher number of groups, as described in further detail hereinbelow.

Optionally, the classifier 130 repeatedly divides the points, into an increasing number of groups, until the classifier 130 successfully verifies that the resultant groups are not intertwined, as described in further detail and illustrated hereinbelow.

Optionally, after the points are divided into a final number of groups, the points in the calculated space constitute a reference set.

The classifier 130 may use the reference set as a criterion, for classifying a new assay of a chemical reaction, as described in further detail and illustrated hereinbelow.

Figure 2:
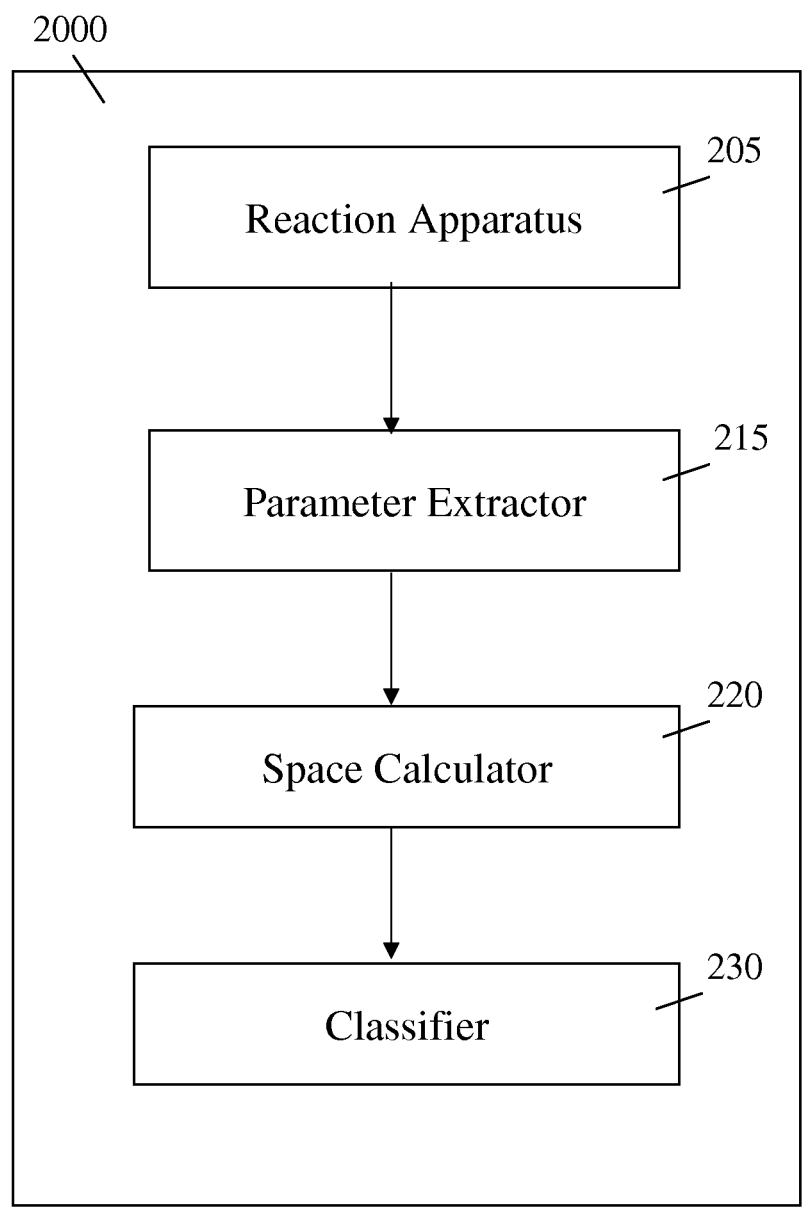
FIG. 2 is a block diagram schematically illustrating a second apparatus for automatic chemical assay classification, according to an exemplary embodiment of the present invention.

Reference is now made to FIG. 2, which is a block diagram schematically illustrating a second apparatus for automatic chemical assay classification according to an exemplary embodiment of the present invention.

Apparatus 2000 for automatic chemical assay classification may be implemented using electric circuits, computer instructions, etc. The apparatus 2000 may be implemented on a dedicated computer, on a computer chip connectable to a laboratory device (say to a PCR apparatus, as known in the art) or installable thereon, on a computerized controller (say a computerized controller used in a chemical factory), etc.

Apparatus 2000 includes a reaction apparatus 205.

The chemical reaction apparatus 205 performs assays of chemical reactions.

Optionally, the reaction apparatus 205 includes a reaction chamber where a chemical reaction may take place, as known in the art.

Optionally, the reaction apparatus 205 further includes one or more sensors, for measuring values of a physical property of the chemical reaction, as known in the art.

For example, the sensors may be photometric sensors installed in proximity of the reaction chamber. The photometric sensors measure intensity of light emitted from the reaction chamber, as the chemical reactions progresses.

The photometric sensors measure the emission of light from the reaction chamber, using standard fluorescence methods, as known in the art.

Optionally, the chemical reactions are Polymerase Chain Reactions (PCR), say Quantitative Fluorescent Polymerase Chain Reactions (QF-PCR), as described in further detail hereinbelow.

Apparatus 2000 further includes a parameter extractor 215, connected to the reaction apparatus 205.

The parameter extractor 215 extracts sets of parameters from the performed assays of the chemical reactions. Each of the received sets of parameters characterizes a specific assay of a chemical reaction.

The extracted parameters may include, but are not limited to: photometric measurement values such as Fluorescence Intensity (FI) values of one or more elbow points of a sigmoid graph depicting the assay of the chemical reaction, a time of each of the elbow points, Fluorescence Intensity (FI) values of certain points of the sigmoid graph, etc., as described in further detail hereinbelow.

Optionally, the parameters include Euclidian Coordinate Values of one or more elbow points of the chemical reaction, as depicted by a graph.

Optionally, the parameters include Euclidian Coordinate Values of at one or more EC50 points of the chemical reaction, as depicted by a graph. An EC50 point is a point halfway between the baseline and maximum of the chemical reaction, as known in the art.

Optionally, the parameter extractor 215 extracts the parameters, using current methods, usable for extracting parameters from a graph which depicts the assay of the chemical reaction, such as PCR, as described in further detail hereinabove.

Apparatus 2000 further includes a space calculator 220, in communication with the parameter extractor 215.

The space calculator 220 calculates a space enhancing proximity among points representative of assays of qualitatively identical chemical reactions. The space calculator 220 further represents each one of two or more of the received sets of parameters, as a respective point in the calculated space.

Methods which may be used by the space calculator 220, for calculating of the space include, but are not limited to: Dimensionality Reduction, Diffusion Mapping and Kernel Principal Component Analysis (Kernel PCA), as described in further detail hereinbelow.

Apparatus 2000 further includes a classifier 230, in communication with the parameter extractor 215.

The classifier 230 divides the points in the calculated space into a number of groups, according to proximity among the points in the calculated space. Each group pertains to a respective chemical reaction. By dividing the points into the groups, the classifier 230 classifies the assays, as described in further detail hereinbelow.

The classifier 230 may uses one or more of standard classification methods, such as K-means clustering, Fuzzy clustering, QT (Quality Threshold) Clustering, Locally-sensitive Hashing, etc., as known in the art.

For example, the classifier 230 may uses k-means clustering, for dividing the points in the calculated space into the number of groups, as described in further detail hereinabove.

Optionally, in order to verify that the groups are not intertwined, the classifier 230 further finds a first point. The first point is a point nearest to a center of a first one of the groups among all points of the first group.

The classifier 230 may also receive first data identifying a chemical reaction of the first point. The first data may include, but is not limited to: data obtained by microbiological testing of the materials used for the assay, data obtained by inspection through a microscope, data extracted using an additional chemical reaction, etc., as known in the art.

The classifier 230 may also find a second point. The second point is a point nearest to a center of a second one of the groups, among all points of the first group.

The classifier 230 may also receive second data identifying a chemical reaction of the second point, say microbiological testing data, as described in further derail hereinabove.

Upon the first and second data indicating a qualitative difference between the chemical reactions of the found points, the classifier 230 divides the points (already divided into the number of groups), into a higher number of groups, as described in further detail hereinbelow.

Optionally, the classifier 230 repeatedly divides the points, into an increasing number of groups, until the classifier 230 successfully verifies that the resultant groups are not intertwined, as described in further detail hereinbelow.

Optionally, after the points are divided into a final number of groups, the points in the calculated space constitute a reference set.

The classifier 230 may use the reference set as a criterion, for classifying a new assay of a chemical reaction, as described in further detail and illustrated hereinbelow.

Figure 3:
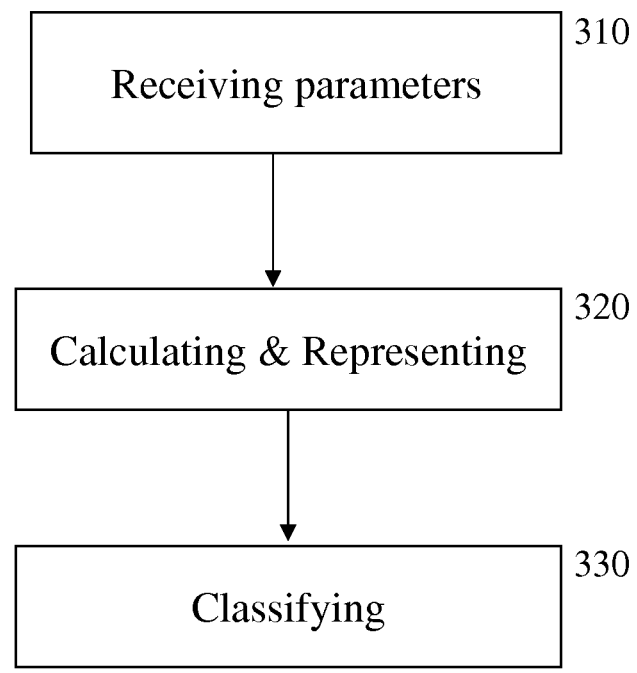
FIG. 3 is a flowchart illustrating a first method for automatic chemical assay classification, according to an exemplary embodiment of the present invention.

Reference is now made to FIG. 3, which is a flowchart illustrating a first method for automatic chemical assay classification, according to an exemplary embodiment of the present invention.

A method for automatic chemical assay classification, according to an exemplary embodiment of the present invention, may be implemented using electric circuits, computer instructions, etc. The method may be implemented on a dedicated computer, on a computer chip connectable to a laboratory device (say to a PCR apparatus, as known in the art) or installable thereon, on a computerized controller (say a computerized controller used in a chemical factory), etc., as described in further detail hereinabove.

Optionally, the chemical reaction is a Polymerase Chain Reaction (PCR), say a Quantitative Fluorescent Polymerase Chain Reaction (QF-PCR), as described in further detail hereinbelow.

According to the exemplary method, there are received 310 sets of parameters, say using the parameter receiver 110, as described in further detail hereinabove. Each one of the received 310 sets of parameters characterizes a specific assay of a chemical reaction.

The received 310 parameters may include, but are not limited to: photometric measurement values such as Fluorescence Intensity (FI) values of one or more elbow points of a sigmoid graph depicting the assay of the chemical reaction, a time of each of the elbow points, Fluorescence Intensity (FI) values of certain points of the sigmoid graph, etc., as described in further detail hereinbelow.

Optionally, the parameters include Euclidian Coordinate Values of one or more elbow points of the chemical reaction, as depicted by a graph, as described in further detail hereinabove.

Optionally, the parameters include Euclidian Coordinate Values of at least one or more EC50 points of the chemical reaction, as described in further detail hereinabove.

Next, there is calculated 320 a space, which enhances proximity among points representative of assays of qualitatively identical chemical reactions, say by the space calculator 120, as described in further detail hereinabove. Each one of two or more of the received 310 sets of parameters is represented 320 as a respective point in the calculated 320 space.

Methods which may be used for calculating 320 the space include, but are not limited to: dimensionality reduction, diffusion mapping and Kernel Principal Component Analysis (Kernel PCA), as described in further detail hereinbelow.

The points in the calculated 320 space are divided into a number of groups, according to proximity among the points in the calculated space, say using the classifier 130, as described in further detail hereinabove. Each of the groups pertains to a respective chemical reaction. By dividing the points into the groups, the classifier 130 classifies 330 the assays, as described in further detail hereinbelow.

Optionally, the points are divided into groups, using one or more of standard classification methods such as K-means clustering, Fuzzy clustering, QT (Quality Threshold) Clustering, Locally-sensitive Hashing, etc., as described in further detail hereinabove.

Optionally, the exemplary method further includes a preliminary step of extracting the parameters from the assay of the chemical reaction, as described in further detail hereinbelow.

Optionally, the parameters are extracted, using current methods usable for extracting parameters from a graph which depicts the assay of the chemical reaction, such as PCR, as described in further detail hereinabove.

Optionally, in order to verify that the groups are not intertwined, there is further found a first point nearest to a center of a first one of the groups, among all points of the first group. There may also be received first data identifying a chemical reaction of the first point.

The first data may include, but is not limited to: data obtained by microbiological testing of the materials used for the assay, data obtained by inspection through a microscope, data extracted using an additional chemical reaction, etc., as known in the art.

There may also be found a second point. The second point is a point nearest to a center of a second one of the groups, among all points of the first group. There may be also received second data identifying a chemical reaction of the second point.

When the first and second data indicates a qualitative difference between the chemical reactions of the found points, the points (already divided into the number of groups) are divided again, into a number of groups higher than the previous number of groups, as described in further detail hereinbelow.

Optionally, the points are repeatedly divided, into an increasing number of groups, until there is verified that the resultant groups are not intertwined, as described in further detail hereinbelow.

Optionally, after the points are divided into a final number of groups, the points in the calculated space constitute a reference set.

The reference set may be used as a criterion, for classifying a new assay of a chemical reaction, as described in further detail and illustrated hereinbelow.

In a first example, upon receiving a new set of parameters characterizing a respective assay of a chemical reaction, the new set is represented as a new point in the calculated 320 space, using out of sample extension. The new point is added to a selected one of the groups. The selected group is a group which has a point nearest to the new point among all points divided into the groups.

In the out of sample extension, the new set of parameters is transformed into the calculated 320 space, without recalculating the space, using an extension method.

For example, the space may be a space calculated 320, using diffusion mapping, and the extension method may be based in Geometric Harmonics, as known in the art.

The assay represented by the new point is thus classified, as belonging to a chemical reaction qualitatively identical to the chemical reactions of the assays represented by the points of the selected group, as described in further detail hereinbelow.

In a second example, the space is recalculated, using the new set of parameters.

The points in the originally calculated 320 space are positioned in the recalculated space, but remain in the groups used for the original classification 330. The new set is represented as a new point in the recalculated space.

Finally, the new point is added to a selected one of the groups. The selected group has a point nearest to the new point among all points divided into the groups.

The assay represented by the new point is thus classified, as belonging to a chemical reaction qualitatively identical to the chemical reactions of the assays represented by the points of the selected group, as described in further detail hereinbelow.

Figure 4:
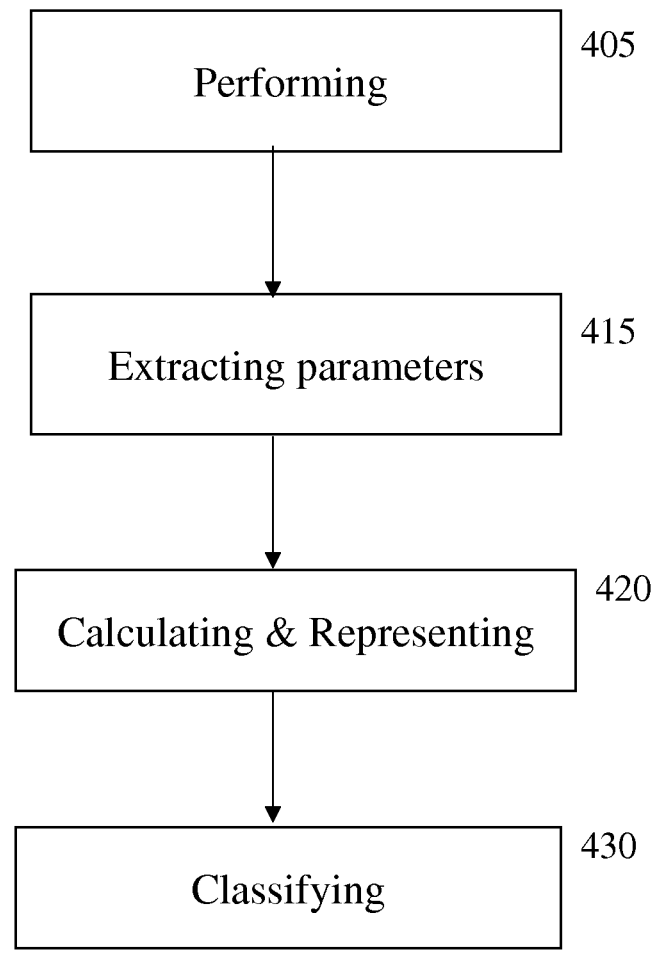
FIG. 4 is a flowchart illustrating a second method for automatic chemical assay classification, according to an exemplary embodiment of the present invention.

Reference is now made to FIG. 4, which is a flowchart illustrating a second method for automatic chemical assay classification, according to an exemplary embodiment of the present invention.

A method for automatic chemical assay classification, according to an exemplary embodiment of the present invention, may be implemented using electric circuits, computer instructions, etc. The method may be implemented on a dedicated computer, on a computer chip connectable to a laboratory device (say to a PCR apparatus, as known in the art) or installable thereon, on a computerized controller (say a computerized controller used in a chemical factory), etc., as described in further detail hereinabove.

Optionally, the chemical reaction is a Polymerase Chain Reaction (PCR), say a Quantitative Fluorescent Polymerase Chain Reaction (QF-PCR), as described in further detail hereinbelow.

According to the exemplary method, assays of chemical reactions, such as Polymerase Chain Reactions (PCR) are performed 405, say using a reaction apparatus 205, as described in further detail hereinabove.

Next, there are extracted 415 sets of parameters, say using the parameter extractor 215, as described in further detail hereinabove. Each one of the extracted 415 sets of parameters characterizes a specific assay of a chemical reaction.

The extracted 415 parameters may include, but are not limited to: photometric measurement values such as Fluorescence Intensity (FI) values of one or more elbow points of a sigmoid graph depicting the assay of the chemical reaction, a time of each of the elbow points, Fluorescence Intensity (FI) values of certain points of the sigmoid graph, etc., as described in further detail hereinbelow.

Optionally, the parameters include Euclidian Coordinate Values of one or more elbow points of the chemical reaction, as depicted by a graph, as described in further detail hereinbelow.

Optionally, the parameters are extracted 415 using current methods, usable for extracting parameters from a graph which depicts the assay of the chemical reaction, as described in further detail hereinabove.

Next, there is calculated 420 a space, which enhances proximity among points representative of assays of qualitatively identical chemical reactions, say by the space calculator 220, as described in further detail hereinabove.

Each one of two or more of the extracted 415 sets of parameters is represented 420 as a respective point in the calculated 420 space.

Methods which may be used for calculating 420 the space include, but are not limited to: dimensionality reduction, diffusion mapping and Kernel Principal Component Analysis (Kernel PCA), as described in further detail hereinbelow.

The points in the calculated 420 space are divided into a number of groups, according to proximity among the points in the calculated space, say using the classifier 230, as described in further detail hereinabove. Each of the groups pertains to a respective chemical reaction. By dividing the points into the groups, the classifier 230 classifies 430 the assays, as described in further detail hereinbelow.

Optionally, the points are divided into the groups using one or more of standard classification methods, such as K-means clustering, Fuzzy clustering, QT (Quality Threshold) Clustering, Locally-sensitive Hashing, etc., as known in the art.

Optionally, in order to verify that the groups are not intertwined, there is further found a first point nearest to a center of a first one of the groups, among all points of the first group, say by the classifier 230.

There may further be received first data identifying a chemical reaction of the first point.

The first data may include, but is not limited to: data obtained by microbiological testing of the materials used for the assay, data obtained by inspection through a microscope, data extracted using an additional chemical reaction, etc., as known in the art.

There may also be found a second point. The second point is a point nearest to a center of a second one of the groups, among all points of the first group.

There may also be received second data identifying a chemical reaction of the second point.

When the first and second data indicates a qualitative difference between the chemical reactions of the found points, the points divided into the number of groups, are divided again, into a number of groups higher than the previous number of groups, as described in further detail hereinbelow.

Optionally, the points are repeatedly divided, into an increasing number of groups, until there is verified that the resultant groups are not intertwined, as described in further detail hereinbelow.

Optionally, after the points are divided into a final number of groups, the points in the calculated space constitute a reference set.

The reference set may be used as a criterion, for classifying a new assay of a chemical reaction, as described in further detail and illustrated hereinbelow.

In a first example, the new set is represented as a new point in the calculated 420 space, using out of sample extension. The new point is added to a selected one of the groups. The selected group is a group, which has a point nearest to the new point among all points divided into the groups.

The assay represented by the new point is thus classified, as belonging to a chemical reaction qualitatively identical to the chemical reactions of the assays represented by the points of the selected group, as described in further detail hereinbelow.

In the out of sample extension, the new set of parameters is transformed into the calculated 420 space, without recalculating the space, using en extension method.

For example, the space may be a space calculated 420, using diffusion mapping, and the extension method may be based in Geometric Harmonics, as known in the art.

In a second example, the space is recalculated, using the new set of parameters.

The points in the originally calculated 420 space are positioned in the recalculated space, but remain in the groups used for the original classification 430. The new set is represented as a new point in the recalculated space.

Finally, the new point is added to a selected one of the groups, which has a point nearest to the new point among all points divided into the groups.

The assay represented by the new point is thus classified, as belonging to a chemical reaction qualitatively identical to the chemical reactions of the assays, represented by the points of the selected group, as described in further detail hereinbelow.

Figure 5:
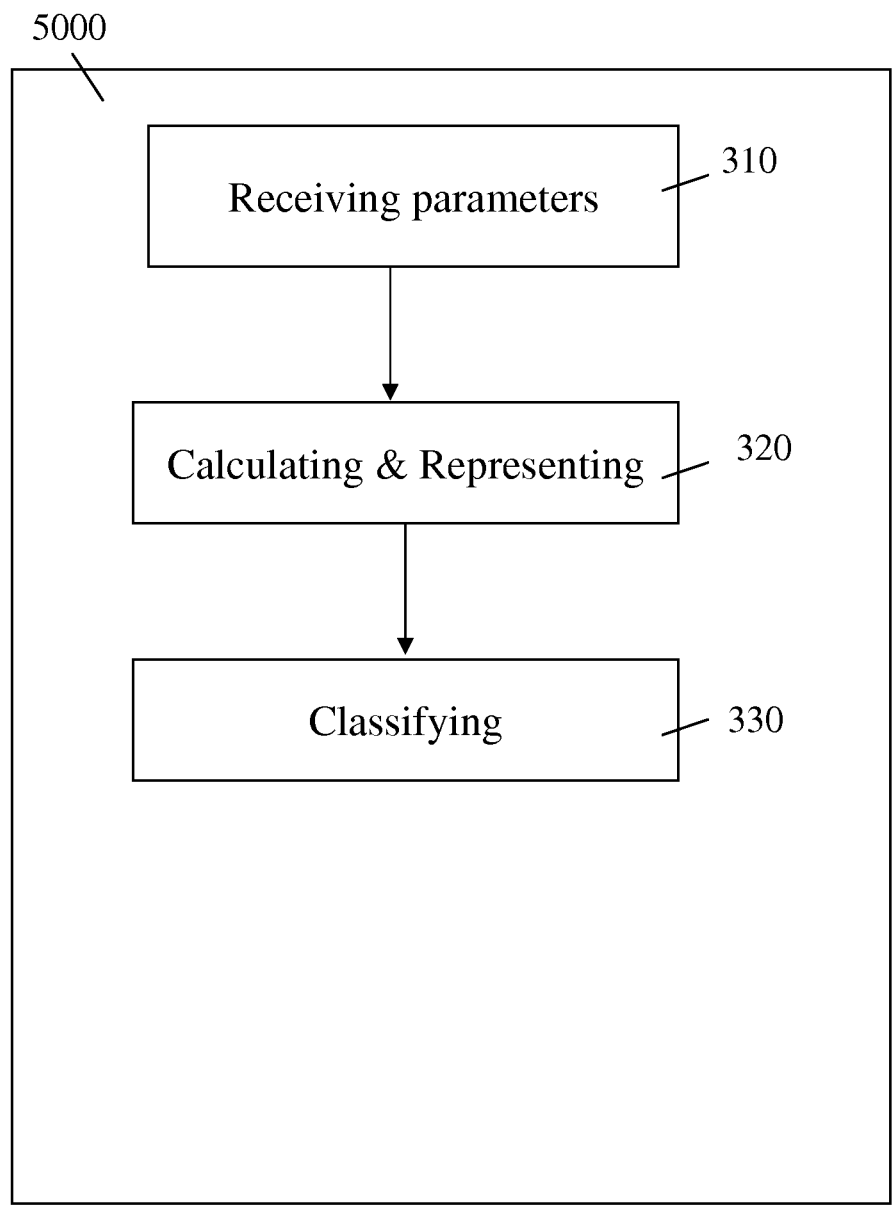
FIG. 5 is a block diagram schematically illustrating a computer readable medium storing computer executable instructions, for performing steps of automatic chemical assay classification, according to an exemplary embodiment of the present invention.

Reference is now made to FIG. 5, which is a block diagram schematically illustrating a computer readable medium storing computer executable instructions for performing steps of automatic chemical assay classification, according to an exemplary embodiment of the present invention.

According to an exemplary embodiment of the present invention, there is provided a computer readable medium 5000 such as a CD-ROM, a USB-Memory, a Portable Hard Disk, a diskette, etc.

The computer readable medium 5000 stores computer executable instructions, performing steps of automatic chemical assay classification, according to an exemplary embodiment of the present invention.

The computer executable instructions may perform steps of one of the exemplary methods described in further detail hereinabove.

According to one exemplary embodiment, the computer readable medium 5000 stores instructions for performing the steps of: receiving 310 the sets of parameters, calculating 320 the space and representing 320 the sets as points in the space, and classifying 330 the assays through dividing the points into the groups, as described in further detail and illustrated, using FIG. 3, hereinabove.

FIG. 6-15 illustrate a method for automatic chemical assay classification, according to an exemplary embodiment of the present invention.

Figure 6:
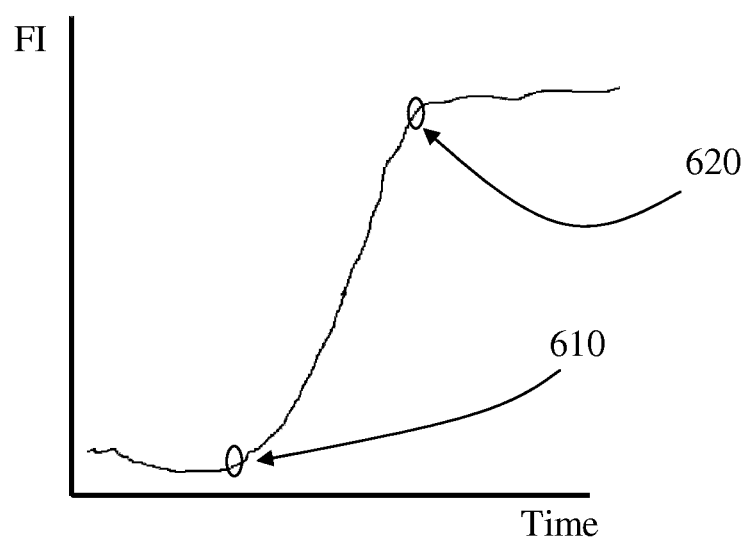
FIG. 6 is an exemplary graph depicting Fluorescence Intensity (FI) values measured over a chemical reaction apparatus, according to an exemplary embodiment of the present invention.

Reference is now made to FIG. 6, which is a first exemplary graph depicting Fluorescence Intensity (FI) values measured over a chemical reaction apparatus, according to an exemplary embodiment of the present invention.

In a method according to an exemplary embodiment of the present invention, there are measured values of a physical property, over a chemical reaction apparatus. For example, an assay of a chemical reaction based on QF-PCR, may be carried out by measuring Fluorescence Intensity (FI) of the QF-PCR based chemical reaction, as known in the art.

The resultant FI values as a function of time may be depicted in a graph, as illustrated in FIG. 6.

In one exemplary scenario, there is extracted a set of parameters from each one of several assays of the chemical reactions, say by the parameter extractor 215, as described in further detail hereinabove.

Optionally, the parameters are extracted, using current methods, usable for extracting parameters from a graph which depicts the assay of the chemical reaction such as PCR, as described in further detail hereinabove.

In one example, in order to extract the parameters, there are identified coordinate values of elbow points of the graph, using currently used techniques, say using US Patent Publication No. 20070148632, to Kurnik et al., or using Int. Patent Application No. PCT/IB2009/053997, to Russak et al.

The set includes a Fluorescence Intensity (FI) value and time of the first elbow point 610 of the chemical reaction. The set further includes an FI value and time of the second elbow point 620 of the chemical reaction.

That is to say that the exemplary scenario is based on four parameters derived from each of the assays of the chemical reactions.

Similarly, there are derived the same four parameters from several other assays, say from hundreds of thousands other assays.

Figure 7:
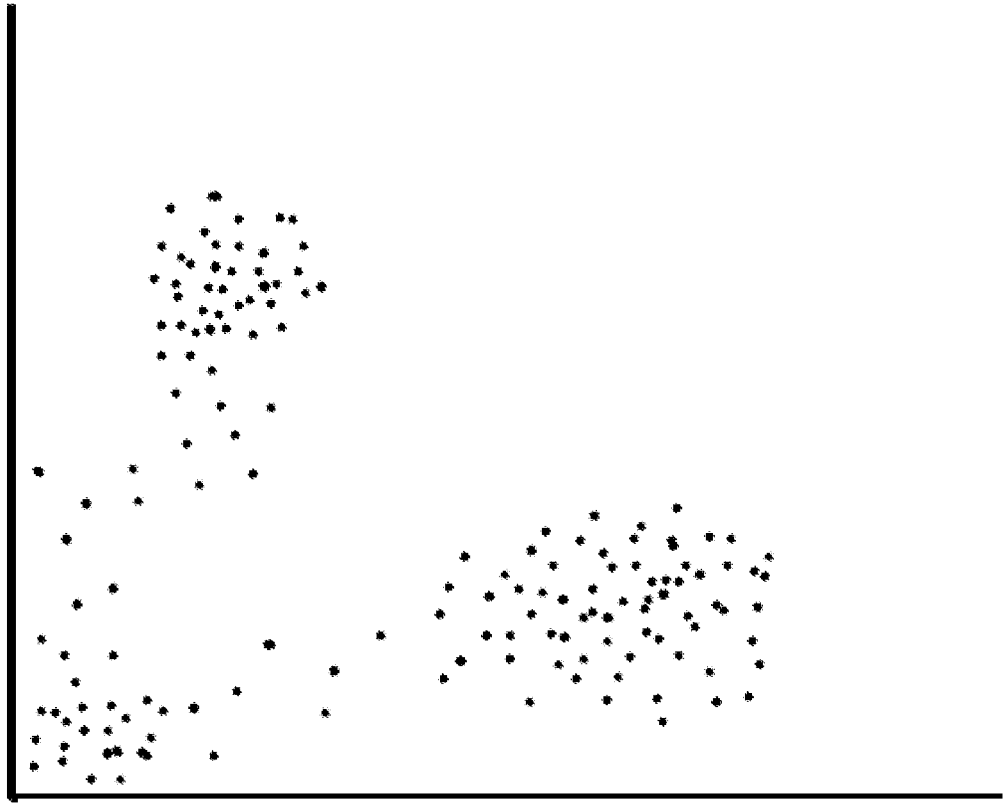
FIG. 7 is an exemplary graph depicting points representing parameters of assays of chemical reactions, derived in accordance with an exemplary embodiment of the present invention, represented in a Euclidian space.

Reference is now made to FIG. 7, which is an exemplary graph depicting points, representing parameters of assays of chemical reactions, derived in accordance with an exemplary embodiment of the present invention, represented in a Euclidian space.

The parameters derived from the chemical reactions may be represented as points in a four-dimensional Euclidian Space. FIG. 7 is a graph which represents a two-dimensional projection of the Four-dimensional Euclidian Space. The two dimensions of FIG. 7 are the Fluorescence Intensity (FI) and time of the first elbow point 610, as described in further detail hereinabove.

Parameters derived from a single type of reaction may assume a wide range of kinetic properties. Hence, data points that represent assays of chemical reactions of the same type may be scattered over a large area in the Euclidian space. That is to say that a Euclidean distance between two data points, which represent assays of the same type of chemical reaction, may be greater than a Euclidean distance between two data points which represent assays of different chemical reaction types.

Consequently, the points which represent the parameters, derived from the assays of the chemical reactions, are distributed over intertwined areas, as shown in FIG. 7. As a result, conventional classification methods may prove ineffective when applied on the points in the Euclidian space.

Figure 8:
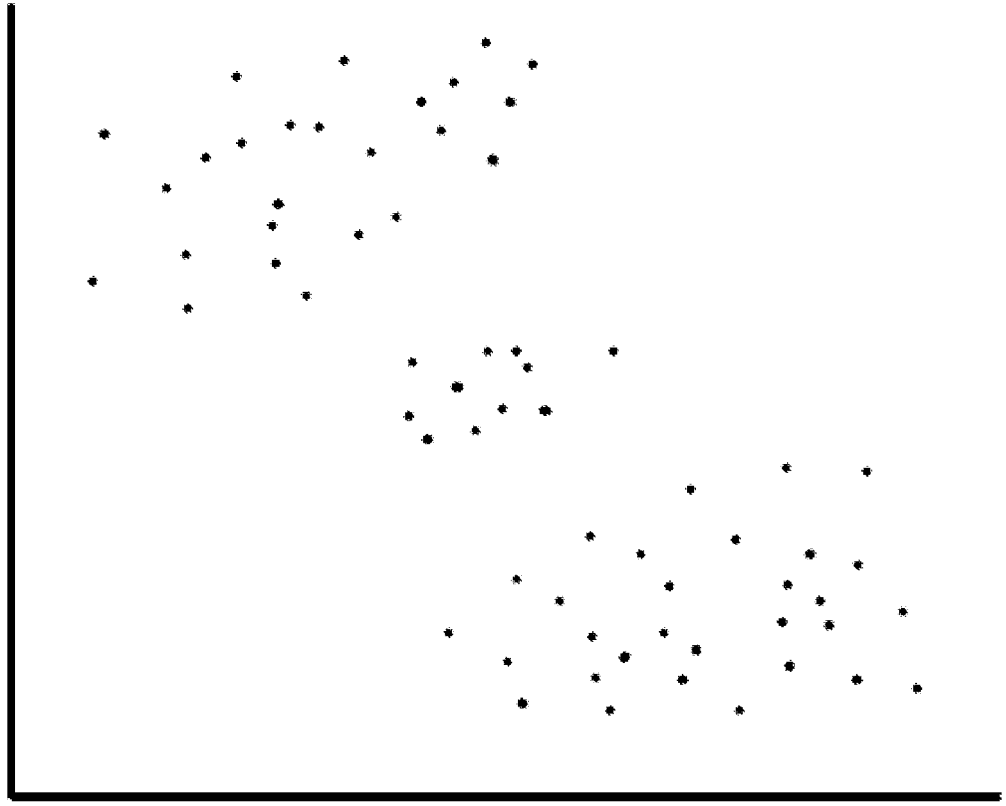
FIG. 8 is an exemplary graph depicting points representing parameters of assays of chemical reactions, represented in a space calculated using diffusion mapping, according to an exemplary embodiment of the present invention.

Reference is now made to FIG. 8, which is an exemplary graph depicting points which represent parameters of assays of chemical reactions, represented in a space calculated, using diffusion mapping, according to an exemplary embodiment of the present invention.

According to an exemplary embodiment of the present invention, there is calculated a space enhancing proximity among points representative of assays of qualitatively identical chemical reactions.

Optionally, the space is calculated by the space calculator 220, as described in further detail hereinabove.

Each one of two or more of the sets of parameters extracted from the chemical assays is represented as a respective point in the calculated space.

Optionally, the space is calculated, using Dimensionality Reduction, also referred to, as Manifold Learning.

Dimensionality Reduction is a process of reducing the number of variables under consideration. Dimensionality Reduction may be divided into Feature Selection and Feature Extraction.

Feature Selection, also known as Variable Selection, Feature Reduction, Attribute Selection or Variable Subset Selection, is a technique, commonly used in machine learning.

With Feature Selection, there is selected a subset of relevant features, for building robust learning models, as known in the art.

In Feature Extraction, when input data to an algorithm is too large to be processed and is suspected to be redundant, the input data is transformed into a reduced representation set of features (also named features vector), as known in the art.

If the features extracted are carefully chosen, it is expected that the features set extracts the relevant information from the input data, in order to perform a desired task, using the resultant reduced representation instead of the whole input data.

Although Dimension Reduction is a technique which usually involves narrowing down the number of dimensions, Dimension Reduction may also involve modifying metrics (say strengthening affinity between points of qualitatively identical chemical reactions), without reducing the number of dimensions.

Examples of quality reduction techniques include, but are not limited to: Diffusion Maps, Anisotropic Maps, Kernel Principal Component Analysis (Kernel PCA), Multi Dimensional Scaling (MDS), Local Linear Embedding (LLE) and Local Multi Dimensional Scaling (Local MDS), as known in the art.

Optionally, the space is calculated, using Diffusion Mapping, as described in further detail and illustrated, using FIG. 13, hereinbelow.

Diffusion Mapping is a recently introduced method of dimensionally reduction, which belongs to a method group known as Kernel Principal Component Analysis (Kernel PCA).

Ronald R. Coifman and Stephane Lafon describe Diffusion Mapping in an article entitled "Diffusion Maps", published in Applied and Computational Harmonic Analysis: Special issue on Diffusion Maps and Wavelets, Vol 21, July 2006, pp 5-30.

Coifman and Lafon show in the article, among other things, that the Diffusion Distance (as defined in the article) in a Euclidean space equals the Euclidean distance (as defined in the article) in a corresponding Diffusion Space.

Diffusion mapping automatically differentiates variable groups in data (such as the sets of parameters described hereinabove), according to how clustered they are.

Diffusion mapping further extracts minimal sets of meaningful variables. The minimal sets describe the input data. All parameters are taken into account. The feature used for differentiation is the level of geometrical separation between the parameters.

By applying diffusion mapping on the Euclidian space, there is calculated a space in which the distance between any two of the points depends on the number of short paths between the two points, as found in the Euclidean space. The distance between the points further depends on the lengths of the short paths.

Short paths connect the two points through a number of points.

Each of the points in the short path may be directly connected only to a point in the connected point's vicinity.

In determining the distance between the two points, the lower is the number of the points connected in the short path, the higher is the weight of the short path.

FIG. 8 is a graph which represents a two-dimensional Space resultant upon applying diffusion mapping on the Euclidian space of FIG. 6. As illustrated using FIG. 8, the two-dimensional Space enhances proximity between points representative of assays of qualitatively identical chemical reactions.

Consequently, the points which represent the parameters, derived from the assays of the chemical reactions, are distributed over clearly separated areas, as shown in FIG. 8. Given the distribution of the points in the clearly separated areas, as a result of the diffusion mapping, classification methods like K-Means Clustering may prove more effective, as described in further detail hereinbelow.

Figure 9:
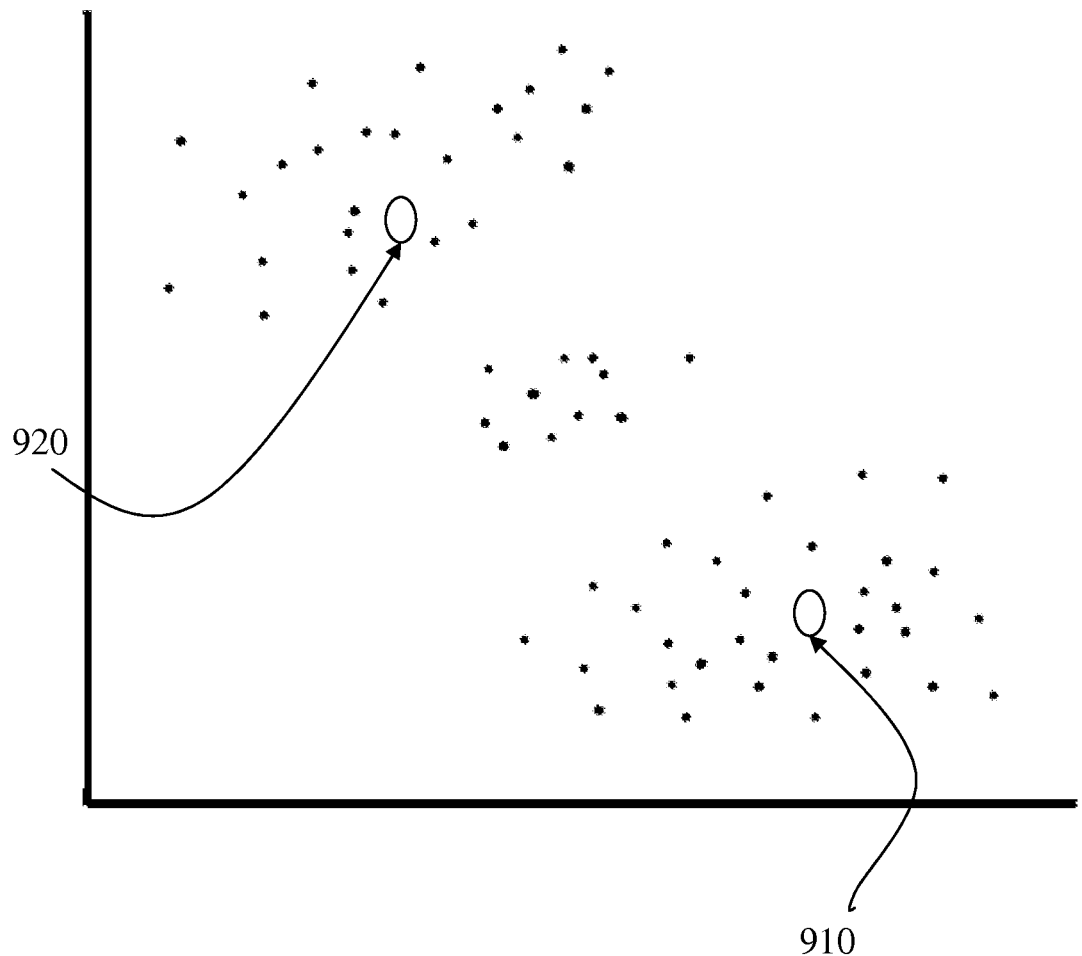
FIG. 9 is an exemplary graph illustrating results of initial K-Means Clustering, according to an exemplary embodiment of the present invention.

Reference is now made to FIG. 9, which is an exemplary graph illustrating results of initial K-Means Clustering, according to an exemplary embodiment of the present invention.

The points in the space calculated using Diffusion Mapping, and illustrated, using FIG. 8, are divided into an initial number of groups, thus classifying the assays represented by the points, say by the classifier 230, as described in further detail hereinabove.

The initial number of groups may be determined by a user of apparatus 2000, say using a Graphical User Interface (GUI), as known in the art.

Alternatively, the initial number of points is a fixed number, say Two.

Optionally, the points are divided into the initial number of groups, by a standard classification method, such as K-Means Clustering, Fuzzy clustering, QT (Quality Threshold) Clustering, Locally-sensitive Hashing, etc., as known in the art.

K-Means Clustering is a method of cluster analysis which aims at partitioning observations into k groups (i.e. clusters).

With K-Means Clustering there are found the centers of the groups in the data. Each of the points belongs to a group with the nearest center.

Each of the centers may be a point which represents a mean of one of the groups (i.e. clusters), or an area which represents points in vicinity of the mean. For example, the center may be an oval area, around a point which represents the mean of the group, as known in the art.

In the exemplary graph of FIG. 9, K-Means Clustering for two groups yields two centers 910, 920.

Next, there is verified that the two groups resultant upon the K-Means Clustering, are not intertwined.

Figure 10:
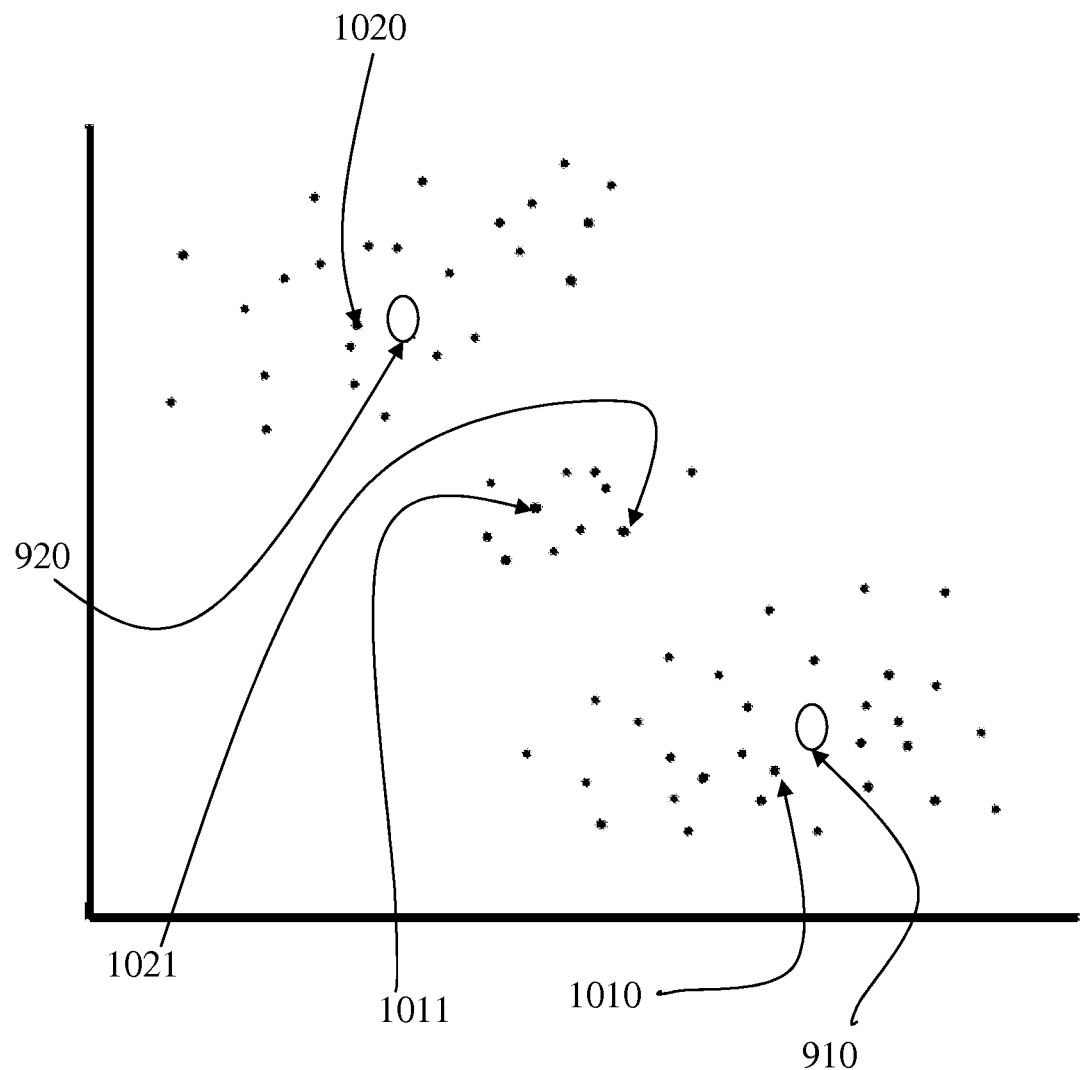
FIG. 10 is an exemplary graph illustrating verifying that groups resultant upon the initial K-Means Clustering, are not intertwined, according to an exemplary embodiment of the present invention.

Reference is now made to FIG. 10, which is an exemplary graph illustrating verifying that the groups resultant upon the initial K-Means Clustering, are not intertwined, according to an exemplary embodiment of the present invention.

Optionally, there is further found a first point 1010. The first point 1010 is a point nearest to a center 910 of a first one of the groups, among all points of the first group.

There may further be received first data identifying the chemical reaction of the first point 1010. The first data may include, but is not limited to: data obtained by microbiological testing of the materials used for the assay represented by the first point 1010, data obtained by inspection through a microscope, data extracted using an additional chemical reaction, etc., as known in the art.

There may also be found a second point 1011. The second point is a point nearest to a center 920 of a second one of the groups, among all points of the first group.

There may also be received second data identifying a chemical reaction of the second point 1011, say data obtained by microbiological testing of the materials used for the assay represented by the second point 1011, as known in the art.

If the first and second data indicates a qualitative difference between the chemical reactions of the found points 1010 and 1011, the points in the space illustrated, using FIG. 8, are divided into an a higher number of groups, say three, as illustrated hereinbelow.

Similarly, there is found a third point 1020. The third point 1020 is a point nearest to the center 920 of the second group among all points of the second group. There may further be received third data identifying the chemical reaction of the third point 1020. The third data may include, but is not limited to data obtained by microbiological testing of the materials used for the assay represented by the third point 1020.

There may also be found a fourth point 1021. The fourth point is a point nearest to a center 910 of the first group, among all points of the second group. There may also be received a fourth data identifying a chemical reaction of the second point 1021, say data obtained by microbiological testing of the materials used for the assay represented by the second point.

If the third and fourth data indicate a qualitative difference between the chemical reactions of the found points 1020 and 1021, the points in the space illustrated, using FIG. 8, are divided into an a higher number of groups, say three, as illustrated hereinbelow.

Figure 11:
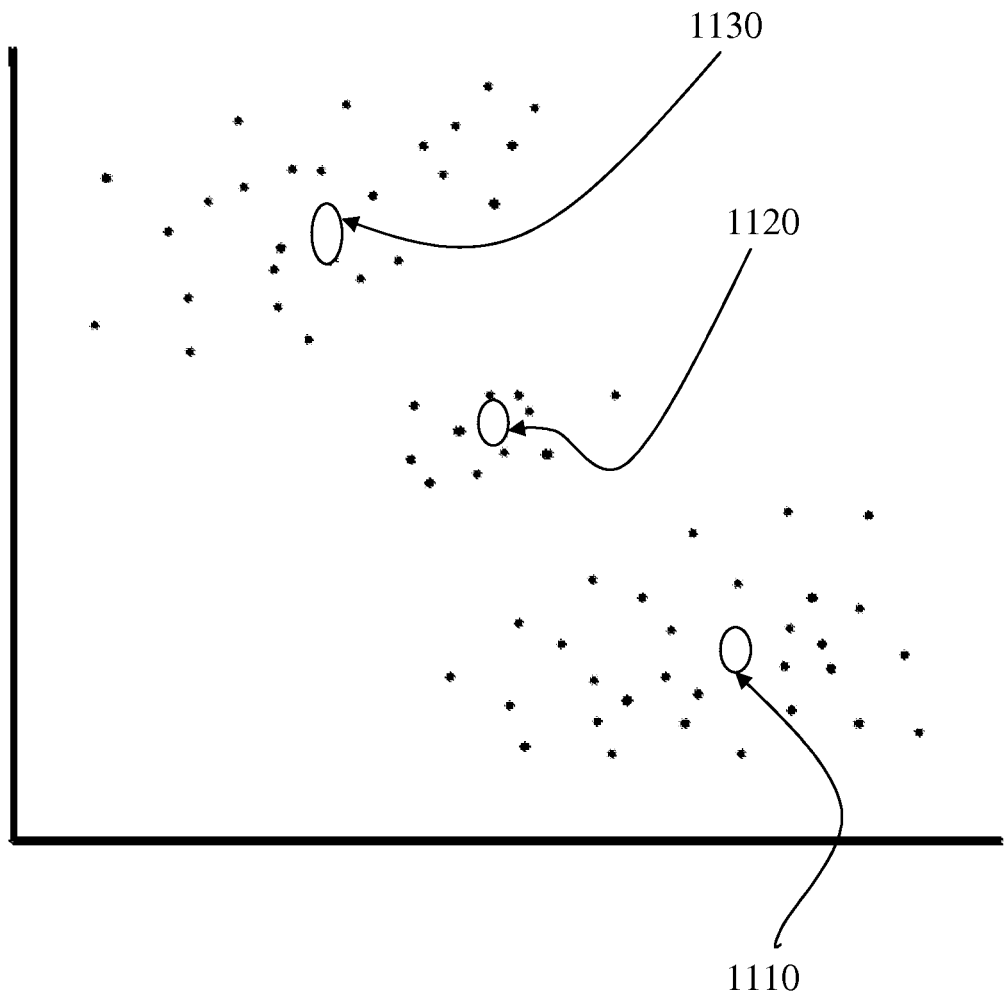
FIG. 11 is an exemplary graph illustrating second K-Means Clustering, according to an exemplary embodiment of the present invention.

FIG. 11 is an exemplary graph illustrating second K-Means Clustering, according to an exemplary embodiment of the present invention.

If case a qualitative difference is found between the points, the points in the space calculated using Diffusion Mapping, and illustrated, using FIG. 8, are divided into a higher number of groups, say to three groups. The points may be divided by the classifier 230, say using K-Means Clustering, as described in further detail hereinabove.

In the exemplary graph of FIG. 11, K-Means Clustering for three groups yields three centers 1110, 1120 and 1130. Each of the centers pertains to one of the three groups.

Next, there is verified that the three groups are not intertwined.

Figure 12:
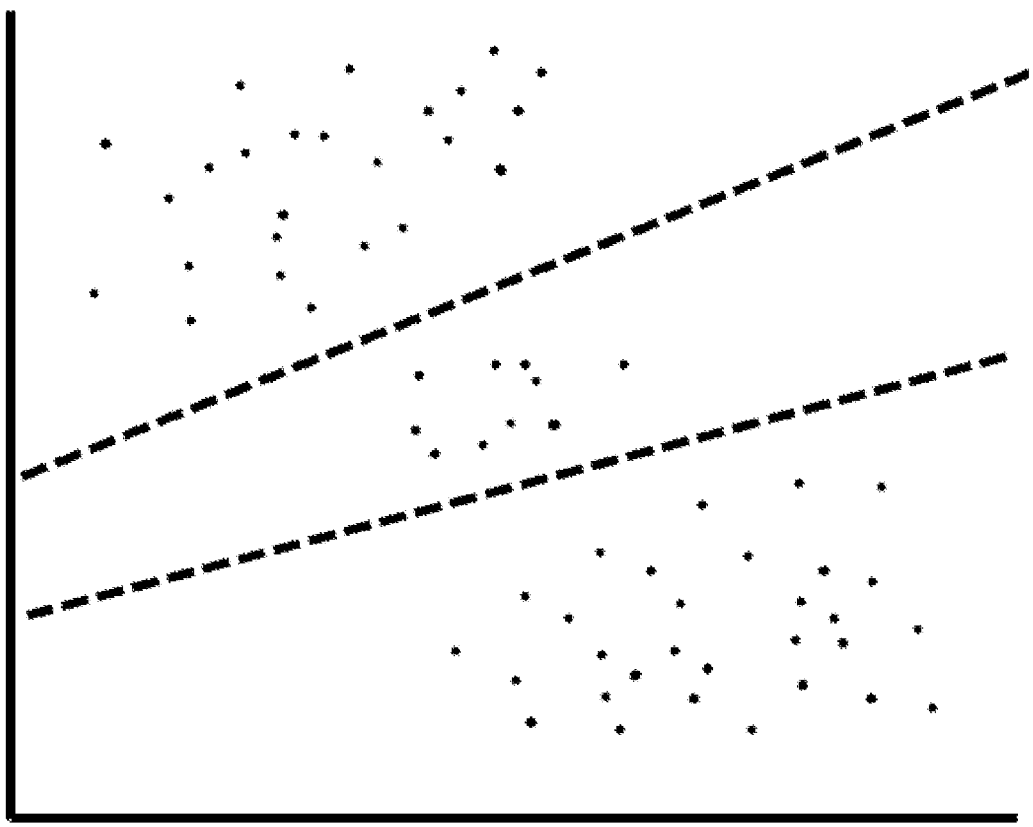
FIG. 12 is an exemplary graph schematically illustrating results of a final classification, according to an exemplary embodiment of the present invention.

Reference is now made to FIG. 12, which is an exemplary graph schematically illustrating results of a final classification, according to an exemplary embodiment of the present invention.

For each of the three groups, there is made a comparison between a point nearest to the group's center and a point nearest to the center of a second one of the groups, among all points of the group.

The comparison may be made using data obtained by microbiological testing, as described in further detail and illustrated using FIG. 10 hereinabove.

Similarly, there is made a comparison between the point nearest to the group's center and a point nearest to a remaining, third one of the groups, among all points of the group. The comparison may be made using data obtained by microbiological testing, as described in further detail and illustrated using FIG. 10 hereinabove.

FIG. 12 illustrates a final classification into three groups, according to an exemplary embodiment of the present invention.

If a qualitative difference is found between the chemical reactions of the points compared, the points in the space illustrated, using FIG. 8, are divided again, into an even higher number, say to four groups.

The process repeats until the space is successfully divided into groups that are not intertwined, i.e. until no qualitative difference is found in the comparisons. Consequently, the classification of the assays is deemed final.

Figure 13:
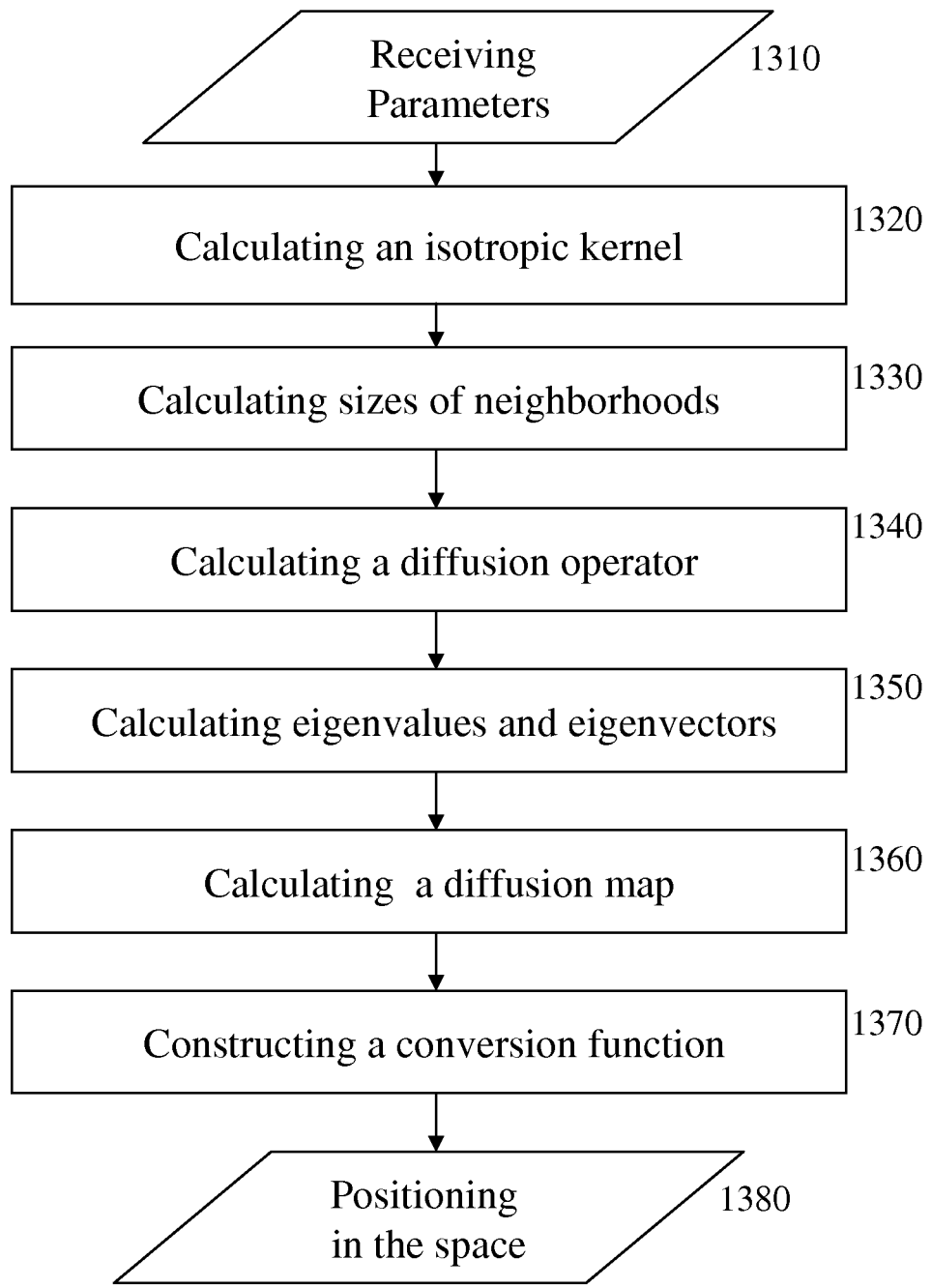
FIG. 13 is a flowchart illustrating an exemplary method for calculating a space and representing parameters in the calculated space, according to an exemplary embodiment of the present invention.

Reference is now made to FIG. 13, which is a flowchart illustrating an exemplary method for calculating a space and representing parameters in the calculated space, according to an exemplary embodiment of the present invention.

The space enhancing proximity among points representative of the assays of qualitatively identical chemical reactions, may be calculated using Diffusion Mapping, say by the space calculator 120, as described in further detail hereinabove.

In one example, there are received 1310 the sets of parameters, say as an input matrix of d columns and n lines. The input matrix contains n sets of d parameters.

Consequently, there is calculated 1320 an isotropic kernel, represented as a matrix of n columns and n lines. Each element in the matrix indicates if respective two of the sets are neighbors.

In one example, two sets of parameters are deemed neighboring, if the Euclidian distance between the two sets is no more than a preset maximal Euclidian distance. Optionally, the maximal Euclidian distance is set by a user of the apparatus 1000.

That is to say that the isotropic kernel defines affinities between the sets of the parameters, which are derived from Euclidian distances among the received 1310 sets.

Next, there are calculated 1330 sizes (also referred to as degrees) of a neighborhood for each one of the sets of parameters, say the number of sets within the preset maximal Euclidian distance from the set.

The calculated 1320 kernel is normalized, using the calculated 1330 sizes, say by dividing each element in the kernel by the size of the element's neighborhood. By normalizing the kernel, there is calculated 1340 a diffusion operator, represented as a matrix of n columns and n lines. The diffusion operator represents the probability of a direct transition between two neighboring ones of the sets (i.e. a transition carried out in a single step, in the Euclidian space, between two neighboring ones of the sets).

Next, there are calculated 1350 eigenvalues and corresponding eigenvectors, for the diffusion operator, say using Singular Value Decomposition, which provides a decomposition of the calculated 1320 kernel into eigenvalues and eigenvectors, as known in the art. Each eigenvector has a corresponding eigenvalue. The eigenvectors are ordered by decreasing values of their corresponding eigenvalues.

Then, a diffusion map is calculated 1360, using a number of highest ones of the calculated 1350 eigenvectors (i.e. eigenvectors which have the highest eigenvalues), say a number selected by a user of apparatus 1000.

Using the eigenvectors, there are provided coordinate values for each of the received 1310 sets of parameters, in a thus calculated space, which, unlike a Euclidian space, enhances proximity between points of higher affinity (i.e. points which represent the qualitatively identical chemical reactions).

The eigenvector has n elements, one for each set of parameters. Each element in the eigenvector sets a single coordinate value for a point, which represents one of the received 1310 sets of parameters. The dimensionality of the calculated space is determined by the number of eigenvectors used for each of the points.

The resultant diffusion map includes the coordinate values set for each of the points in the calculated space which enhances proximity among points representative of qualitatively identical chemical reactions.

The calculated 1360 diffusion map is used to construct 1370 a conversion function, which defines the calculated space, which enhances proximity among points representative of assays of qualitatively identical chemical reactions. That is to say that the conversion function is based, at least on each of the point's coordinate values, as included in the diffusion map.

Optionally, the conversion function further includes an out of sample extension method, usable for representing a new set of parameters in the space. The out of sample extension method may be based on Geometric Harmonics, as known in the art. The out of sample extension methods provides coordinate values, for the new point.

The conversion function's diffusion map is used to position 1380 the points in the calculated space, thus representing each of the received 1310 sets of parameters, in the calculated space, as described in further detail and illustrated hereinabove.

Optionally, the out of sample extension method is used to represent a new set of parameters, in the space, as described in further detail hereinabove. Alternatively, upon receiving the new set, the diffusion map is calculated again, using steps 1310-1360, and a new conversion function is constructed, as describe in further detail hereinabove.

As described by Coifman and Lafon, and explained in further detail hereinabove, the Euclidean distance in the calculated space is determined by the number of short paths between parameter sets (represented by points). The more paths there are between two sets, in the Euclidean space, and the shorter the paths are, the closer the points are in the calculated space.

According to an exemplary embodiment of the present invention, the length of a path may be determined by the number of sets (i.e. the number of steps) on the path, where each set may be directly connected only to the neighbors of the set, as defined by the diffusion operator.

The more sets (and thus steps) the path is comprised of, the more differences are needed to accumulate, in order to indicate a change from one reaction type to another. Conversely, the more points the calculated space includes, the lower is the number of paths between the corresponding sets and the more sets are found on each path.

Consequently, a great distance between points, in the calculated space, indicates a difference between reaction types of the parameter sets represented by each of the distant points.

It is expected that during the life of this patent many relevant PCR devices and systems will be developed and the scope of the terms herein, particularly of the terms "Polymerase Chain Reaction", "Quantitative Fluorescent Polymerase Chain Reaction", "Fluorescence" and "Computer", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A computer implemented method for automatic chemical assay classification, the method comprising steps the computer is programmed to perform, the steps comprising:
    on a computer processor, receiving a plurality of sets of parameters, each one of the received sets of parameters characterizing a respective assay of a chemical reaction;
    calculating a space enhancing proximity among points representative of assays of qualitatively identical chemical reactions, and representing each one of at least two of the received sets of parameters as a respective point in the calculated space; and
    dividing the points in the calculated space into a number of groups, according to proximity among the points in the calculated space, each group pertaining to a respective chemical reaction, thereby classifying the assays.

2. The method of claim 1, wherein said calculating the space is carried out using a Kernel Principal Component Analysis (Kernel PCA).

3. The method of claim 1, wherein said calculating the space is carried out using diffusion mapping.

4. The method of claim 1, wherein the chemical reaction is a Polymerase Chain Reaction (PCR).

5. The method of claim 1, further comprising a preliminary step of extracting the parameters from the assay of the chemical reaction.

6. The method of claim 1, wherein the parameters comprise Euclidian Coordinate Values of at least one elbow point of the chemical reaction.

7. The method of claim 1, wherein the parameters comprise Euclidian Coordinate Values of at least one EC50 point of the chemical reaction.

8. The method of claim 1, further comprising finding a first point being nearest to a center of a first group among all points of the first group, receiving first data identifying a chemical reaction of the first point, finding a second point being nearest to a center of a second group among all points of the first group, receiving second data identifying a chemical reaction of the second point, and upon the first and second data indicating a qualitative difference between the chemical reactions of the found points, dividing the points divided into the number of groups, into a higher number of groups.

9. The method of claim 1, further comprising after said dividing and upon receiving a Previously Presented set of parameters characterizing a respective assay of a chemical reaction, representing the Previously Presented set as a Previously Presented point in the calculated space, using out of sample extension, and adding the Previously Presented point to a selected one of the groups, the selected group having a point nearest to the Previously Presented point among all points divided into the groups.

10. The method of claim 1, further comprising after said dividing and upon receiving a Previously Presented set of parameters characterizing a respective assay of a chemical reaction, recalculating the space, repositioning the points divided into the groups in the recalculated space, representing the Previously Presented set as a Previously Presented point in the recalculated space and adding the Previously Presented point to a selected one of the groups, the selected group having a point nearest to the Previously Presented point among all points divided into the groups.

11. An apparatus for automatic chemical assay classification, the apparatus comprising:
    a computer processor;
    a parameter receiver, implemented on the computer processor, configured to receive a plurality of sets of parameters, each one of the received sets of parameters characterizing a respective assay of a chemical reaction;
    a space calculator, in communication with said parameter receiver, configured to calculate a space enhancing proximity among points representative of assays of qualitatively identical chemical reactions, and to represent each one of at least two of the received sets of parameters as a respective point in the calculated space; and
    a classifier, in communication with said spaces calculator, configured to divide the points in the calculated space into a number of groups, according to proximity among the points in the calculated space, each group pertaining to a respective chemical reaction, thereby classifying the assays.

12. The apparatus of claim 11, wherein said space calculator is further configured to calculate the space, using a Kernel Principal Component Analysis (Kernel PCA).

13. The apparatus of claim 11, wherein said space calculator is further configured to calculate the space, using diffusion mapping.

14. The apparatus of claim 11, wherein the chemical reaction is a Polymerase Chain Reaction (PCR).

15. The apparatus of claim 11, further comprising a parameter extractor, in communication with said parameter receiver, configured to extract the parameters from the assay of the chemical reaction.

16. The apparatus of claim 11, wherein the parameters comprise Euclidian Coordinate Values of at least one elbow point of the chemical reaction.

17. The apparatus of claim 11, wherein said classifier is further configured to find a first point being nearest to a center of a first group among all points of the first group, receive first data identifying a chemical reaction of the first point, find a second point being nearest to a center of a second group among all points of the first group, receive second data identifying a chemical reaction of the second point, and upon the first and second data indicating a qualitative difference between the chemical reactions of the found points, to divide the points divided into the number of groups, into a higher number of groups.

18. The apparatus of claim 11, wherein said computer processor is a part of a device installable in connection with a laboratory device.

19. An apparatus for automatic chemical assay classification, the apparatus comprising:
- a chemical reaction apparatus, configured to perform a plurality of assays of chemical reactions;
- a parameter extractor, implemented on a computer processor connected to said chemical reaction apparatus, configured to extract a set of parameters from each of the performed assays;
- a space calculator, in communication with said parameter receiver, configured to calculate a space enhancing proximity among points representative of assays of qualitatively identical chemical reactions, and to represent each one of at least two of the extracted sets of parameters as a respective point in the calculated space; and
- a classifier, in communication with said spaces calculator, configured to divide the points in the calculated space into a number of groups, according to proximity among the points in the calculated space, each group pertaining to a respective chemical reaction, thereby classifying the assays.

20. A tangible computer readable medium storing computer executable instructions for performing steps of automatic chemical assay classification, the steps comprising:
- receiving a plurality of sets of parameters, each one of the received sets of parameters characterizing a respective assay of a chemical reaction;
- calculating a space enhancing proximity among points representative of assays of qualitatively identical chemical reactions, and representing each one of at least two of the received sets of parameters as a respective point in the calculated space; and
- dividing the points in the calculated space into a number of groups, according to proximity among the points in the calculated space, each group pertaining to a respective chemical reaction, thereby classifying the assays.

* * * * *